(12) United States Patent
Franken et al.

(10) Patent No.: US 7,161,040 B2
(45) Date of Patent: Jan. 9, 2007

(54) METHOD FOR PREPARATION OF CARBORANE ANIONS

(75) Inventors: Andreas Franken, Boulder, CO (US); Benjamin T. King, Reno, NV (US); Josef Michl, Boulder, CO (US)

(73) Assignee: The Board of Regents of the University and Community College System of Nevada on Behalf of the University of Nevada Reno, Reno, NV (US)

( * ) Notice: Subject to any disclaimer, the term of this patent is extended or adjusted under 35 U.S.C. 154(b) by 381 days.

(21) Appl. No.: 10/472,329

(22) PCT Filed: Apr. 1, 2002

(86) PCT No.: PCT/US02/10060

§ 371 (c)(1), (2), (4) Date: Jul. 2, 2004

(87) PCT Pub. No.: WO02/079210

PCT Pub. Date: Oct. 10, 2002

(65) Prior Publication Data

US 2004/0242934 A1    Dec. 2, 2004

Related U.S. Application Data

(60) Provisional application No. 60/280,243, filed on Mar. 30, 2001.

(51) Int. Cl.
C07C 331/00 (2006.01)
C07C 335/00 (2006.01)
C07C 381/00 (2006.01)

(52) U.S. Cl. .............................. 568/1; 568/4
(58) Field of Classification Search .................... 568/1, 568/4
See application file for complete search history.

(56) References Cited

U.S. PATENT DOCUMENTS 3,526,650 A    9/1970    Young .................. 260/429
5,731,470 A    3/1998    Michl et al. ............... 564/9
6,180,829 B1    1/2001    Strauss et al. ............ 568/3

OTHER PUBLICATIONS

King et al. Chemical innovation, Dec. 2001, p. 23-31.*
G. Dunks et al., *A one-step synthesis of $B_{11}H_{14}$ ion from $NaBH_4$*, Inorg. Chem. 17(6):1514-1516, 1978.
M. Fein et al., *Carboranes. II. The preparation of 1- and 1,2-substituted carboranes*, Inorg. Chem. 2(6):1115-1119, 1963.
W. Knoth et al., *C-amminecarbaundecaborane(12) derivatives and cesium tridecahydro-carbaundecaborate(1-)*, Inorg. Synth. 11:33-41, 1968.
J. Michl, *Carboranes: Useful tools in physical organic chemistry*, Abstract, 221$^{st}$ ACS meeting, San Diego, California, Mar. 30-Apr. 4, 2001.
K. Nestor et al., *Ten-vertex monocarbaborane chemistry. 17. A convenient new preparation of [closo-1-$CB_9H_{10}$]-anion and the crystal and molecular structure of [($\eta^5$-$C_5Me_5$)$_{Ir_2}$2 $Cl_3$]+[closo-1-$CB_9H_{10}$]-*, Collect. Czech. Chem. Commun. 57(6):1262-1268, 1992.
J. Plesek et al., *A convenient preparation of 1-$CB_{11}H_{12}$ and its C-amino derivatives*, Collect. Czech. Chem. Commun. 49(7):1559-1562, 1984.

* cited by examiner

*Primary Examiner*—Thurman K. Page
*Assistant Examiner*—Yevgeny Valenrod
(74) *Attorney, Agent, or Firm*—Greenlee, Winner, and Sullivan, P.C.

(57) ABSTRACT

This invention relates to an improved method for making unsubstituted carborane anions and monosubstituted carborane anions of formula: $(R-CB_n-H_{m'})^-$ where n is an integer ranging from 5 to about 11 and m' is an integer ranging from 5 to 16 where the relative values of n and m' depend upon the exact structure of the carborane and the presence of a non-hydrogen substituent. m as used herein is an integer ranging from 5 to 16. When R is hydrogen the anion is unsubstituted. When R is a halogen, a phenyl, a substituted phenyl group, such as fluorophenyl group, or any other substituent, the carborane is substituted. The method is particularly useful for preparation of twelve-vertex carborane anions $R-CB_{11}H_{11}^-$, where R is a defined above, and is specifically useful for preparation of the unsubstituted carborane $CB_{11}H_{12}$-??, where R is H.

26 Claims, No Drawings

METHOD FOR PREPARATION OF CARBORANE ANIONS

CROSS-REFERENCE TO RELATED APPLICATIONS

This application is the National Stage of International Application No. PCT/US02/10060, filed Apr. 1, 2002, which claims the benefit of U.S. provisional application Ser. No. 60/280,243, filed Mar. 30, 2001, which is hereby incorporated by reference to the extent not inconsistent herewith.

STATEMENT REGARDING FEDERALLY SPONSORED RESEARCH OR DEVELOPMENT

This invention was made with U.S. Government support under National Science Foundation Grant No. 981979. The Government has certain rights in this invention.

BACKGROUND OF THE INVENTION

It is generally known that salts of the twelve-vertex carborane anion $CB_{11}H_{12}^-$ (I) serve as starting materials for the preparation of partially and fully substituted anions of the type $CB_{11}X_nH_{(12-n)}^-$ (II, where the substituents X need not be the same). The latter are of considerable interest as relatively inert and weakly nucleophilic anions for applications including, among others, incorporation in catalysts for olefin polymerization, incorporation in lithium cation battery electrolytes, and incorporation in radioactive waste treatment materials. The most common choices of substituent X for such applications are X=halogen, X=alkyl, and X=halogenated alkyl, e.g. trifluoromethyl.

Carborane anions, such as II, are described in U.S. Pat. No. 5,731,470, which is incorporated by reference in its entirety herein. This patent describes synthesis of these anions (II) from the corresponding unsubstituted anion (I). The patent also discusses the use of carborane anions in batteries and electrochromic displays.

Until the present time, the high cost of the starting material, $CB_{11}H_{12}^-$, has discouraged commercial use of these highly promising anions. As far as we are aware, this starting material is at present sold commercially by only one company (Katchem Ltd., Prague, Czech Republic), and is very expensive. Currently the anion is produced from an expensive precursor, decaborane, in three steps; the synthesis is difficult to scale up and is performed in small batches.

The present invention provides a method for making unsubstituted anions (I) and related unsubstituted and monosubstituted carborane anions at significantly lower cost. The new synthetic method provided makes the use of these anions, and substituted anions, such as II, practical for commercial applications.

SUMMARY OF THE INVENTION

This invention relates to an improved method for making unsubstituted carborane anions and monosubstituted carborane anions of formula:

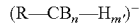

where n is an integer ranging from 5 to about 11 and m' is an integer ranging from 5 to 16 where the relative values of n and m' depend upon the exact structure of the carborane and the presence of a non-hydrogen substituent. m as used herein is an integer ranging from 5 to 16. When R is hydrogen the anion is unsubstituted. When R is a halogen, a phenyl, a substituted phenyl group, such as a fluorophenyl group, or any other substituent, the carborane is substituted. The method is particularly useful for preparation of twelve-vertex carborane anions $R\text{---}CB_{11}H_{11}^-$, where R is as defined above, and is specifically useful for preparation of the unsubstituted carborane $CB_{11}H_{12}^-$, where R is H.

The synthetic method involves reaction of a borane anion $B_nH_m^-$ with a carbene $(Y^1Y^2C:)$ preferably, but not necessarily, in the presence of a strong base. Although not wishing to be bound by any particular mechanism, it is believed that the carbene inserts into a borane dianion $B_nH_{m'-1}^{2-}$ which is generated from the starting borane monoanion by the action of strong base. The strong base can serve a dual function, in that it can also be instrumental in the generation of the carbene $(Y^1Y^2C:)$. Exemplary strong bases useful in this reaction include hydride, e.g., provided as NaH, or organolithium compounds (e.g., including alkyl or aromatic lithium compounds), such as n-butyllithium.

A salt of the starting borane anion $(B_nH_m)^-M^+$ is dissolved or partially dissolved in an appropriate solvent, preferably an ether. The choice of cation employed depends at least in part on the solvent employed and is compatible with the reagents used as discussed below. When desired, strong base is added to the reaction mixture at this point. A carbene $Y^1Y^2C:$ where one or both of $Y^1$ and $Y^2$ can be a halide or another substituent such as a phenyl group or a substituted phenyl group is generated and inserts into the borane cage giving the carborane anion to generate $CB_nH_{m'}^-$, (where R is H) particularly when both $Y^1$ and $Y^2$ are both chlorides and a strong base was present, and $R\text{---}CB_nH_{m'}^-$ when other choices of $Y^1$ and $Y^2$ are made (for example, when one or both of $Y^1$ and $Y^2$ are R) or when strong base was absent. Depending on the nature of the substituent R, it resides either in position 1 of the carborane cage of the product, i.e., on the carbon atom (e.g., when R is phenyl), or in position 2, i.e., on a boron that is located next to the carbon atom (e.g., when R is bromine).

Carbenes useful in the reactions of this invention can be generated by a variety of methods that are well known in the art. Dichlorocarbene is of particular use in the synthesis of $CB_{11}H_{12}^-$. Dichlorocarbene is generated for example, in chloroform by the action of strong base, as is well known in the art. Halocarbenes and dihalocarbenes are generally preferred for use in these syntheses.

A preferred base is NaH combined with a small amount of an alcohol such as methanol or ethanol, which is converted into a well soluble sodium alkoxide, assuring smooth dichlorocarbene formation from chloroform. A small amount of a side product $R\text{---}CB_nH_{m'}^-$ in which R is alkoxy, located in position 2, is then also formed, but can be removed easily because its salts are quite soluble in water. When nitrogen bases, includes amines, are present in the carbene insertion reaction mixtures, they have a much stronger tendency to appear as substituents in the carborane anion products. Nitrogen bases are, thus, not suitable for use as strong bases in the reactions of this invention unless a nitrogen-containing substituent is desired (e.g., in the $CB_{11}H_{12}^-$ product, this substituent will appear in position 2). It is often desirable to handle the starting borane anions in the form of salts with certain alkylamines that have good solubility in solvents, such as tetrahydrofuran (THF) and dimethyl ether (DME), employed in the reactions of this invention. The cations of nitrogen bases can be used in the starting borane salts of this invention, particularly those of nitrogen bases that are volatile, however, care must be taken to convert the starting borane into a salt with another cation such as $Na^+$ first and to substantially remove any nitrogen base thus avoiding its presence in the carbene insertion reaction mixture to avoid undesirable substitution.

Solvents for the reaction and the addition of cations to the reaction mixture are selected to avoid premature precipitation of borane anions or borane dianions and decreased yields of desired products For example, it is believed that no reaction of $B_{11}H_{14}^-$ was observed when 1,4-dioxane was used as the solvent because the disodium salt of $B_{11}H_{13}^{2-}$ is barely soluble in this solvent.

The carborane anion products are isolated from the reaction mixture as salts $R-CB_nH_m^--M^+$. Preferred cations $M^+$ are alkylammonium cations, such as trialkyl ammonium cations which are added after completion of the reaction.

In a specific embodiment, the methods of this invention are employed in the synthesis of the carborane $CB_{11}H_{12}^-$. Salts of this twelve-vertex carborane anion can be prepared in about 40% yield from inexpensive and readily available materials in a single step. The procedure can be completed in one day and can be readily scaled up. The presently preferred synthetic reaction involves an insertion of dichlorocarbene into the eleven-vertex borane anion $B_{11}H_{14}^-$ (presumably, as discussed above, in the form of the dianion, $B_{11}H_{13}^{2-}$, produced in the presence of a strong base). The sodium salt of $B_{11}H_{14}^-$ is a preferred starting material, however, this salt can be difficult to handle and when dry, ignites spontaneously in air. The sodium salt of $B_{11}H_{14}^-$ can be formed in situ by initial addition of a soluble salt in which the cation is a cation of a volatile base, such as an alkylamine, followed by removal of the volatile base under reduced pressure. A preferred cation for the preparation of these salts in situ is the trimethylammomium cation. This is also the preferred cation for isolation of the salt of the product from the reaction mixture.

In a preferred embodiment, the product salt $(CB_{11}H_{12})^-$ $(CH_3)_3NH^+$ is formed in high purity, about 98%. The only detectable impurity (2%) in the isolated product is the 2-chloro derivative of the desired product, $2\text{-Cl}-CB_{11}H_{11}^-$ (where substituents are numbered as is conventional in the art). For most intended applications the product salt can be employed without further purification. Art-known methods, such as preparative HPLC or exploitation of differential solubility (the trimethylammonium salt of the 2-chloro substituted anion is more soluble in water than the parent anion), can be employed for further purification if desired.

In yet other specific embodiments, carbenes other than dichlorocarbene can be used to generate the unsubstituted anion or its variously substituted derivatives such as $1\text{-R}-CB_{11}H_{11}^-$, where R, for example, is a phenyl group or a substituted phenyl group.

Salts of the starting borane anion, $B_{11}H_{14}^-$, are well-known and readily synthesized by known methods. The trimethylammonium salt can be readily synthesized in one step from inexpensive commercially available precursors, sodium borohydride ($NaBH_4$) and boron trifluoride ($BF_3$).

Other borane anions can also be used and provide access to additional carborane anions, such as $CB_9H_{12}^-$. The method of synthesis of this invention, thus is not limited to a single carbene and single borane anion, and is general.

The invention is further illustrated by the following non-limiting examples.

DETAILED DESCRIPTION OF THE INVENTION

Synthesis of $[Me_3NH]^+[CB_{11}H_{12}]^-$: from $[Me_3NH]^+$ $[B_{11}H_{14}]^-$; $CCl_2$ from $CHCl_3/NaH+EtOH$, medium scale. In a 2 L two-neck flask $[Me_3NH]^+[B_{11}H_{14}]^-$[1] (20 g, 0.104 mol) was dissolved in THF (200 mL) under an argon atmosphere. The solution was cooled to 0° C. and NaH (95%) (23 g, 1 mol) was added carefully. After stirring 30 min at room temperature, the THF and $NMe_3$ were removed in vacuum and THF (400 mL) and $CHCl_3$ (30 ml, 0.375 mol) were added. The reaction mixture was stirred for 2 h at ambient temperature. EtOH (80 ml) were added dropwise at 0° C. and it was stirred for 4 h at room temperature. Water (600 mL) was added and the THF was removed in vacuum and the solution was acidified by addition of 10% HCl. Residual THF and EtOH were removed in vacuum. $[Me_3NH]^+Cl^-$(20 g, 0.2 mol) was added, and a white solid precipitated, which was dried in vacuum to yield a colorless mixture of $[Me_3NH]^+[CB_{11}H_{12}]^-$(8.9 g, 42%) containing 2% of a $[Me_3NH]^+[2\text{-Cl-1-}CB_{11}H_{12}]^-$ contaminant as judged by $^{11}B$ NMR.

Synthesis of $[Me_3NH]^+[CB_{11}H_{12}]^-$: $CCl_2$ from $CHCl_3/NaH+EtOH$. In a 250 mL two-neck flask $[Me_3NH]^+$ $[B_{11}H_{12}]^-$(1 g, 5.2 mmol) was dissolved in THF (10 mL) under an argon atmosphere. The solution was cooled to 0° C. and NaH (95%) (1.0 g, 44 mmol) was added carefully. After stirring 15 min at room temperature, the THF and $NMe_3$ were removed under reduced pressure and THF (20 mL) and $CHCl_3$ (1.5 ml, 18.8 mmol) were added. The reaction mixture was stirred briefly (up to 1 h; this makes no difference) at ambient temperature. EtOH (4mL) was added dropwise at 0° C. and the mixture was stirred for 2 h at room temperature.

$H_2O$ (30 mL) was added, the THF and EtOH were removed under reduced pressure and the solution was acidified by addition of 10% HCl. $[Me_3NH]^+Cl^-$(1 g, 10 mmol) was added, and a white solid precipitated, which was dried under reduced pressure to yield colorless $[Me_3NH]^+$ $[CB_{11}H_{12}]^-$(445 mg, 42%); by $^{11}B$ NMR analysis, this contains a 2% impurity of $[Me_3NH]^+[2\text{-Cl-1-}CB_{11}H_{12}]$.

$[Me_4NH]^+Cl^-$(0.5 g, 4.6 mmol) was added to the filtrate, and a white precipitate was separated and dried under reduced pressure. The residue was dissolved in methanol (6 mL) and filtered. The filtrate was injected on a HPLC and a 50/50 $MeOH/H_2O$ mixture was used to separate [2-(EtO)-1-$CB_{11}H_{11}]^-$($R_F$=16.7). Methanol was removed from the eluate under reduced pressure and the residual aqueous solution was extracted three times with diethyl ether (40 mL). The combined ether extracts were evaporated to dryness and the colorless oil was dissolved in water (50 mL). After addition of a solution of $[Me_3NH]^+Cl^-$(0.5 g, 4.6 mmol) in $H_2O$ (20 mL), the white precipitate was filtered and dried under reduced pressure to yield $[Me_4N]^+[2\text{-EtO-}1\text{-}CB_{11}H_{12}]^-$(67 mg, 5%).

Synthesis of $[Me_3NH]^+[CB_{11}H_{12}]^-$: $CCl_2$ from EtOH/$NaH+CHCl_3$. In a 250 mL two-neck flask $[Me_3NH]^+$ $[B_{11}H_{14}]^-$[1](1 g, 5.2 mmol) was dissolved in THF (10 mL) under an argon atmosphere. The solution is cooled to 0° C. and NaH (95%) (1.0 g, 44 mmol) was added carefully. After stirring 15 min at room temperature, the THF and $NMe_3$ were removed in vacuum and THF (20 mL) was added. EtOH (1 mL, 16 mmol) and afterwards $CHCl_3$ (1.5 ml, 18.8 mmol) were added dropwise at 0° C. The reaction mixture was stirred for 1 h at ambient temperature.

EtOH (3 ml) and $H_2O$ (30 mL) were added, the THF and EtOH were removed in vacuum and the solution was acidified by addition of 10% HCl. $[Me_3NH]^+Cl^-$(1 g, 10 mmol) was added, and a white solid precipitated, which was dried in vacuum to yield colorless $[Me_3NH]^+[CB_{11}H_{12}]^-$(445 mg, 42%) containing a 2% impurity of $[Me_3NH]^+[2\text{-Cl-1-}CB_{11}H_{12}]^-$ as judged by $^{11}B$ NMR.

The addition of the CHCl$_3$ in the last two experiments was conducted at different temperatures (−30° C., 0° C., 67° C.). It was shown that the yields were not improved by using different temperatures.

Synthesis of [Me$_3$NH]$^+$[CB$_{11}$H$_{12}$]$^-$: CCl$_2$ from EtOH/NaH+CHCl$_3$. In a 250 mL three-neck flask Me$_3$NH$^+$B$_{11}$H$_{14}^-$ (5.0 g, 0.026 mol) was dissolved in THF (50 mL) under an argon atmosphere. After cooling to 0° C. NaH (95%, 2.00 g, 0.088 mol) was added slowly. After warming up to room temperature stirring was continued for 30 min. The mixture was evaporated to dryness under reduced pressure and THF (100 mL) was added. The resulting mixture was cooled to 0° C. and NaOEt (4.42 g, 0.0650 mol) was added. Over a period of 2.5 h CHCl$_3$ (3.1 mL, 0.039 mol) was added. The reaction mixture was allowed to warm to room temperature over a period of 18 h. The solvent was evaporated and water (100 mL) was added. The solution was acidified by the addition of 10% HCl (20 mL). Residual THF and EtOH were removed under reduced pressure. Charcoal (1 g) was added to the solution and stirred for 5 min., then the solid material was filtered off. After addition of Me$_3$NHCl (5 g, 0.05 mol) to the filtrate a white solid (3.19 g) precipitated. The solid was then dissolved in 2 N NaOH (50 mL) and stirred for 2 h. The basic layer was extracted with Et$_2$O (3×30 mL) and the solvent removed under reduced pressure. The resulting oil was dissolved in water (30 mL) and Me$_3$NHCl (5 g. 0.05 mol) was added. The compound was purified by column chromatography on silica gel (180 g, column 3.5×20 cm, CH$_2$Cl$_2$/MeCN=4: 1, R$_f$=0.31) to yield Me$_3$NH$^+$CB$_{11}$H$_{12}^-$ (1.63 g, 30%).

Synthesis of [NMe$_3$H]$^+$[CB$_{11}$H$_{12}$]$^-$: CCl$_2$ from EtONa/NaH+CHCl$_3$. In a 500 mL three-neck flask Me$_3$NH$^+$B$_{11}$H$_{14}^-$ (5 g, 26 mmol) was dissolved in THF (100 mL) under argon atmosphere. The solution was cooled to 0° C. and NaH (95%, 1.45 g, 60 mmol) was added slowly. After stirring for 30 min at 0° C. the cooling was removed and the mixture was evaporated to dryness under reduced pressure and THF (150 mL) was added. NaOEt (6.80 g, 100 mmol) was added to the reaction flask and the mixture was again cooled to 0° C. CHCl$_3$ (5.20 mL, 70 mmol) was added over a period of 11 h. The reaction mixture was stirred for 1 h at 0° C. and then slowly warmed to room temperature. Water (100 mL) was added and THF was evaporated under reduced pressure. The solution was acidified by the addition 10% HCl (40 mL). Residual THF and EtOH were removed under reduced pressure. Charcoal (2 g) was added and the solution was stirred for an additional 15 minutes at which time the solid material was filtered off. Upon the addition of Me$_3$NHCl to the supernatant (5 g, 50 mmol) a white solid precipitated. The solid was dried under reduced pressure to yield a mixture of [Me$_3$NH]$^+$[CB$_{11}$H$_{12}$]$^-$ and [Me$_3$NH]$^+$[CB$_{11}$H$_{11}$OEt]$^-$(2.40 g), with a ratio of products of approximately 3:1, respectively. A small amount of Me$_3$NH$^+$B$_{11}$H$_{14}$ (<5%) was also present in the isolated material. The material was dissolved in methanol (20 mL) and water (50 mL) was added. The solution was boiled until its volume was 35–40 mL and allowed to cool slowly to room temperature and then placed in the refrigerator overnight. A white solid crystallized. The solution was filtered and NMe$_3$H$^+$CB$_{11}$H$_{12}^-$ (0.770 g, 4 mmol, ~92% purity) was collected. The supernatant was again heated to boiling and the volume reduced to 30–35 mL. The solution was allowed to cool to room temperature and placed in the refrigerator for several h. Upon cooling a solid crystallized from the solution. Filtration yielded [Me$_3$NH]$^+$[CB$_{11}$H$_{11}$OEt]$^-$(0.300 g, 1 mmol, ~85% purity).

The NMe$_3$H$^+$CB$_{11}$H$_{12}^-$ product (0.770 g, 4 mmol) was added to a 50 mL saturated aqueous solution of CsOH and allowed to stir for 3 h after which time the solid in the solution was collected by filtration. The filtrate was washed with acetone and again the solids were filtered. Evaporation of the acetone yielded Cs$^+$CB$_{11}$H$_{12}^-$(0.350 g, 1 mmol, ~95% pure). The material insoluble in the acetone was dissolved in HCl (10%, 10 mL) and upon the addition of Me$_3$NHCl (0.100 g, 1 mmol) a solid precipitate formed. The solid collected was Me$_3$NH$^+$B$_{11}$H$_{14}^-$(0.090 g 0.4 mmol). The CsOH solution was extracted with ether/acetone (70/30, 3×75 mL) to yield additional Cs$^+$CB$_{11}$H$_{12}^-$(0.200 g, 0.7 mol, ~98–99% pure).

Synthesis of [Me$_3$NH]$^+$[CB$_{11}$H$_{12}$]$^-$: CCl$_2$ from CHCl$_3$/NaH+MeOH. In a 250 mL two-neck flask [Me$_3$NH]$^+$[B$_{11}$H$_{14}$]$^-$[1](1 g, 5.2 mmol) was dissolved in THF (10 mL) under an argon atmosphere. The solution was cooled to 0° C. and NaH (95%) (1.0 g, 44 mmol) was added carefully. After stirring 15 min at room temperature, the THF and NMe$_3$ were removed in vacuum and THF (20 mL) and CHCl$_3$ (1.5 mL, 18.8 mmol) were added. The reaction mixture was stirred briefly (up to 1 hr; this makes no difference) 1 h at ambient temperature. MeOH (4 mL) was added dropwise at 0° C. and the stirring was continued for 2 h at room temperature.

H$_2$O (30 mL) was added, the THF and MeOH were removed under reduced pressure and the solution was acidified by addition of 10% HCl. [Me$_3$NH]$^+$Cl$^-$ (1 g, 10 mmol) was added, and a white solid precipitated, which was dried under reduced pressure to yield colorless [Me$^3$NH]$^+$[CB$_{11}$H$_{12}$]$^{31}$ (445 mg, 42%); by $^{11}$B NMR analysis, this contains a 2% impurity of [Me$_3$NH]$^+$[2-Cl-1-CB$_{11}$H$_{12}$]$^-$.

[Me$_4$N]$^+$Cl$^-$ (0.5 g, 4.6 mmol) was added to the filtrate, and a white precipitate was separated and dried under reduced pressure. The residue was dissolved in methanol (6 mL) and filtered. The filtrate was injected on an HPLC and a 50/50 MeOH/H$_2$O mixture was used to separate [2-MeO-1-CB$_{11}$H$_{11}$]$^-$ (R$_F$=16.7). Methanol was removed from the eluate under reduced pressure and the residual aqueous solution was extracted three times with diethyl ether (40 mL). The combined ether extracts were evaporated to dryness and the colorless oil was dissolved in water (50 mL). After addition of a solution of [Me$_4$H]$^+$[Cl]$^-$ (0.5 g, 4.6 mmol) in H$_2$O (20 mL), the white precipitate was filtered and dried under reduced pressure to yield [Me$_4$N]$^+$[2-(MeO)-1-CB$_{11}$H$_{12}$]$^-$ (64 mg, 5%). Another byproduct, [Me$_4$N]$^+$[2-CCl$_2$H—CB$_{11}$H$_{11}$]$^-$ is also formed (2%).

Synthesis of [Me$_3$NH]$^+$[CB$_{11}$H$_{12}$]$^-$: CCl$_2$ from CHCl$_3$+NaOH. In a 250 mL two-neck flask [Me$_3$NH]$^+$[B$_{11}$H$_{14}$]$^-$[1] (1 g, 5.2 mmol) was dissolved in H$_2$O (20 mL) with NaOH (0.5 g, 12.5 mmol) under an atmosphere of argon. After stirring 1 h at room temperature, the H$_2$O was removed in vacuum and THF (20 mL) was added. The reaction mixture was cooled to −78° C. and CHCl$_3$ (2 mL, 24 mmol) was added. The reaction mixture was allowed to stir over night at ambient temperature.

The THF was removed in vacuum and the residue was taken up in 50 mL of water, and the solution was acidified by addition of 10% HCl. After addition of [Me$_3$NH]$^+$Cl$^-$ (1 g, 10 mmol) a white solid precipitated, which yielded after drying in vacuum a colorless mixture of [Me$_3$NH]$^+$[CB$_{11}$H$_{12}$]$^-$ (270 mg, 22%), [Me$_3$NH]$^+$[B$_{11}$H$_{14}$]$^-$(370 mg, 37%), and [Me$_3$NH]$^+$[2-Cl-1-CB$_{11}$H$_{12}$]$^-$ (75 mg, 5%), as judged by $^{11}$B NMR.

Synthesis of [Me$_3$NH]$^+$[CB$_{11}$H$_{12}$]$^-$: CCl$_2$ from CHCl$_3$+BuLi, neat NaB$_{11}$H$_{14}$. In a 250 mL two-neck flask [Na]$^+$[B$_{11}$H$_{14}$]$^-$ [1] (1 g, 6.4 mmol) was dissolved in THF (20 mL)

under an argon atmosphere. The solution was cooled to −78° C. and n-BuLi (7.5 mL, 12 mmol) was added dropwise. After stirring 1 h at room temperature the solution was cooled to −78° C. and CHCl$_3$ (2 mL, 24 mmol) was added, and the reaction mixture was allowed to stir over night at ambient temperature.

The THF was removed in vacuum and the residue was taken up in 50 mL of water. The solution was acidified by addition of 10% HCl and after addition of [Me$_3$NH]+Cl$^-$ (1 g, 10 mmol) a white solid precipitated, which was dried under reduced pressure to yield a colorless mixture of [Me$^3$NH]$^+$[CB$_{11}$H$_{12}$]$^-$ (280 mg, 22%) and [Me$_3$NH]$^+$[2-Cl-1-CB$_{11}$H$_{12}$]$^-$ (75 mg, 5%) as judged by $^{11}$B NMR. It can be difficult to isolate and handle the dry sodium salt of [B$_{11}$H$_{14}$]$^-$. Na[B$_{11}$H$_{14}$] forms solvates with solvents, and in its dry form it spontaneously ignites in air. K[B$_{11}$H$_{14}$]$^-$ and Me$_4$N[B$_{11}$H$_{14}$]$^-$ salts have very limited solubility in solvents like THF, and therefore they are not very useful for these reactions.

Synthesis of [Me$_3$NH]$^+$[CB$_{11}$H$_{12}$]$^-$: CCl$_2$ from CHCl$_3$+ BuLi, NaB$_{11}$H$_{14}$ made in situ. In a 250 mL two-neck flask [Me$_3$NH]$^+$[B$_{11}$H$_{14}$]$^-$[1] (1 g, 5.2 mmol) was dissolved in THF (20 mL) under an argon atmosphere. The solution was cooled to −78° C. and n-BuLi (4 mL, 6.4 mmol) was added dropwise. After stirring 1 h at room temperature the solvent was removed in vacuum and THF (20 mL) was added. The solution was cooled to −78° C. and (8 mL, 12.8 mmol) n-BuLi was added. After stirring 1 h at room temperature the solution was cooled to −78° C. and CHCl$_3$ (2 ml, 24 mmol) were added. The reaction mixture was allowed to stir overnight at ambient temperature. The THF was removed in vacuum and the residue was taken up in 50 mL of H$_2$O. The solution was acidified by addition of 10% HCl. After addition of [Me$_3$NH]$^+$Cl$^-$(] g, 10 mmol) a white solid precipitated, which was dried in vacuum to yield a colorless mixture of [Me$_3$NH]$^+$[CB$_{11}$H$_{12}$]$^-$(290 mg, 27%) and [Me$_3$NH]$^+$[B$_{11}$H$_{14}$]$^-$ (320 mg, 32%), as judged by $^{11}$B NMR.

The Use of Different Strong Bases:

Other bases such as NaOMe, NaOEt, NaOBu$^t$, NaOH, amyl sodium were used in addition to NaH and BuLi. The yields of isolated [Me$_3$NH]$^+$[CB$_{11}$H$_{12}$]$^-$ with these other bases were around 10% and by far not as good as with NaH.

The use of Solvents Other than THF:

Synthesis of [Me$_3$NH]$^+$[CB$_{11}$H$_{12}$]$^-$ DME as solvent. In a 250 mL two-neck flask [Me$_3$NH]$^+$[B$_{11}$H$_{14}$]$^-$[1] (1 g, 5.2 mmol) was dissolved in DME (10 mL) under an argon atmosphere. The solution was cooled to 0° C. and NaH (95%) (1.0 g, 44 mmol) was added carefully. After stirring 15 min at room temperature, the THF and NMe$_3$ were removed in vacuum and DME (20 mL) and CHCl$_3$ (1.5 ml, 18.8 mmol) were added. The reaction mixture was stirred for 1 h at ambient temperature. EtOH (4 mL) was added dropwise at 0° C. and it was stirred for 2 h at room temperature.

H$_2$O (30 mL) was added, the DME and EtOH were removed in vacuum and the solution was acidified by addition of 10% HCl. [Me$_3$NH]$^+$Cl$^-$ (1 g, 10 mmol) was added, and a white solid precipitated, which was dried under reduced pressure to yield a colorless mixture of [Me$_3$NH]$^+$[CB$_{11}$H$_{12}$]$^-$ (425 mg 38%) containing [Me$_3$NH]$^+$[2-Cl-1-CB$_{11}$H$_{12}$]$^-$ as a 2% impurity, as judged by $^{11}$B NMR.

Synthesis of [Me$_3$NH]$^+$[CB$_{11}$H$_{12}$]$^-$: diglyme as solvent. In a 250 mL two-neck flask [Me$_3$NH]$^+$[B$_{11}$H$_{14}$]$^-$[1] (1 g, 5.2 mmol) was dissolved in diglyme (10 mL) under an argon atmosphere. The solution was cooled to 0° C. and NaH (95%) (1.0 g, 44 mmol) was added carefully. After stirring 15 min at room temperature, the THF and NMe$^3$ were removed in vacuum, and diglyme (20 mL) and CHCl$_3$ (1.5 ml, 18.8 mmol) were added. The reaction mixture was stirred for 1 h at ambient temperature. EtOH (4 mL) was added dropwise at 0° C. and it was stirred for 2 h at room temperature. H$_2$O (30 mL) was added, the diglyme and the EtOH were removed in vacuum and the solution was acidified by addition of 10% HCl. [Me$_3$NH]$^+$Cl$^-$ (1 g, 10 mmol) was added, and a white solid precipitated, which was dried under reduced pressure to yield a colorless mixture of [Me$_3$NH]$^+$[CB$_{11}$H$_{12}$]$^-$ (200 mg, 19%) and colorless [Me$_3$NH]$^+$[2-Cl-1-CB$_{11}$H$_{12}$]$^-$ (37 mg, 3%), as judged by $^{11}$B NMR. When 1,4 dioxane was used under the conditions as described for diglyme, only unreacted [Me$_3$NH]$^+$ [B$_{11}$H$_{14}$]$^-$ was obtained, because the Na$_2$[B$_{11}$H$_{13}$] is barely soluble in 1,4 dioxane.

Synthesis of [Me$_3$NH]$^+$[2-Cl-1-CB$_{11}$H$_{12}$]$^-$: CCl$_2$ from PhHgCCl$_3$ (note: no base present; it appears from this experiment that the presence of a base is essential to avoid 2-substitution). Into a 25 mL two-neck flask with [Me$_3$NH]$^+$ [B$_{11}$H$_{14}$]$^-$(100 mg, 0.5 mmol), and PhHgCCl$_3$ (2 g, 5 mmol) diglyme (5 mL) was added, and the mixture was heated overnight at 130° C. under an argon atmosphere. After cooling down to room temperature, the diglyme solution was transferred to a separation funnel and H$_2$O (25 mL) was added. The water layer was extracted three times with diethyl ether (25 mL) and the ether layers were separate and combined. The ether was removed in vacuum and the diglyme was removed in a Kugelrohr. The residue was dissolved in methanol (3 mL) and filtered. The filtrate was injected on a HPLC and a 50/50 MeOH/H$_2$O mixture was used to separate unreacted starting material [B$_{11}$H$_{14}$]$^-$ (R$_F$=13) (49 mg, 49%) from [2-Cl-1-CB$_{11}$H$_{11}$]$^-$(R$_F$=17.5).

The methanol was removed in vacuum from the combined MeOH/H$_2$O/[2-Cl-1-CB$_{11}$H$_{11}$]$^-$ fraction. The aqueous solution was extracted three times with diethyl ether (20 mL) and the organic layers were separated from the aqueous layer. The combined ether extracts were evaporated to dryness and the colorless oil was dissolved in water (40 mL). After addition of [Me$_4$N]$^+$[Cl]$^-$ (0.1 g, 1 mmol) in H$_2$O (20 mL), the white pure [Me$_4$N]$^+$[2-Cl-1-CB$_{11}$H$_{11}$]$^-$ was filtered and dried in vacuum to yield (20 mg, 20%). When corrected for the recovered starting material, the yield of the 2-chloro derivative is 40%.

Synthesis of [2-Me$_3$N-1-CB$_{11}$H$_{12}$]$^-$: CCl$_2$ from CHCl$_3$+ n-BuLi and neat [Me$_3$NH]$^+$[B$_{11}$H$_{14}$]$^-$ (note: in the presence of amine nucleophiles, position 2 is substituted). In a 250 mL two-neck flask [Me$_3$NH]$^+$[B$_{11}$H$_{14}$]$^-$[1] (1 g, 5.2 mmol) was dissolved in THF (20 mL) under an argon atmosphere. The solution was cooled to −78° C. and n-BuLi (10 mL, 16 mmol) was added dropwise. After stirring 1 h at room temperature, the solution was cooled to −78° C. and CHCl$_3$ (2 mL, 24 mmol) was added, and the reaction mixture was allowed to stir over night at room temperature.

The THF was removed in vacuum and the residue was taken up in 50 ml of water, and the solution was acidified by addition of 10% HCl. A yellow solid was filtered and washed three times with 10 mL portions of water and dried in vacuum to yield pale yellow [2-Me$_3$N-1-CB$_{11}$H$_{12}$] (200 mg, 19%). [Me$_3$NH]$^+$Cl$^-$ (1 g, 10 mmol) was added to the filtrate, a white solid was filtered, washed three times with 10 mL portions of water and dried in vacuum to recover colorless starting material [Me$_3$NH]$^+$[B$_{11}$H$_{14}$]$^-$ (300 mg, 30%).

It appears very important to substantially remove trimethylamine from the reaction mixture under reduced pressure if unsubstituted product is to be made. Most of the nitrogen bases attack and substitute the 2-position of $[CB_{11}H_{12}]^-$. Therefore all nitrogen containing bases were excluded in the investigations.

Separation of $[Me_3NH]^+[CB_{11}H_{12}]^-$ from $[B_{11}H_{14}]^-$ (in case of incomplete carbene insertion reaction). In a 250 mL flask with 2N NaOH (50 mL) a mixture of $[Me_3NH]^+$ $[B_{11}H_{14}]^-$ (400 mg, 2.1 mmol) and $[Me_3NH]^+[CB_{11}H_{12}]^-$ (600 mg, 2.9 mmol) were added and stirred for 1 h at room temperature. The $Me_3N$ was removed in vacuum and the strong alkaline solution was extracted three times with diethylether (30 mL). The ether from the combined ether extracts was removed in vacuum and the oil was dissolved in $H_2O$ (50 mL). The solution was acidified by addition of 10% HCl and after addition of $[Me_3NH]^+Cl^-$ (0.5 g, 5 mmol) a white solid precipitated, which was filtered and dried in vacuum to yield pure colorless $[Me_3NH]^+$ $[CB_{11}H_{12}]^-$ (570 mg, 95%).

The use of other carbenes besides $CCl_2$:

Synthesis of $[Me_4N]^+[CB_{11}H_{11}]^-$ and $[Me_4N]^+[2-Br-1-CB_{11}H_{11}]^-$: $CBr_2$ from $CHBr_3+NaOEt/NaH^-$ ($CBr_2$ inserts but over half of the product contains a bromine substituent in position 2). In a 250 mL two-neck flask $[Me_3NH]^+$ $[B_{11}H_{14}]^-$ (1 g, 5.2 mmol) was dissolved in dry THF (20 mL) under an argon atmosphere. The solution was cooled to 0° C., and NaH (95%) (1.2 g, 53 mmol) was added. After stirring 15 min at room temperature, the THF and the $Me_3N$ was removed in vacuum. THF (40 mL) was added to the residue, the suspension was cooled to 0° C., and $CHBr_3$ (2 mL, 22.9 mmol) was added.

The reaction mixture was stirred over night at room temperature. Ethanol (10 mL) was added slowly to the mixture. After addition of water (20 mL), the THF and the ethanol were removed in vacuum and 1N NaOH (100 mL) was added. The solution was transferred to a separation funnel, and the alkaline solution was extracted three times with diethyl ether (25 mL) and the ether layers were separated from the aqueous layer. The combined ether extracts were evaporated to dryness and the pale yellow oil was dissolved in methanol (5 mL) and filtered. The filtrate was injected on a HPLC and a 53/47 MeOH/$H_2O$ mixture was used to separate the desired $[CB_{11}H_{12}]^-(R_F=15)$ from the byproduct $[2-Br-1-CB_{11}H_{11}]^-(R_F=23)$.

The methanol was removed under reduced pressure from the combined MeOH/$H_2O$ fractions containing $[CB_{11}H_{12}]^-$ and the aqueous solution was extracted three times with diethyl ether (40 mL). The combined ether extracts were evaporated to dryness and the colorless oil was dissolved in water (50 mL). After addition of a solution of $[Me_4N]^+[Cl]^-$ (0.5 g, 4.6 mmol) in $H_2O$ (20 mL), the white $[Me_4N]^+$ $[CB_{11}H_{12}]^-$ was filtered and dried in vacuum to yield (0.15 g, 14%).

The methanol was removed under reduced pressure from the combined MeOH/$H_2O$ fractions containing $[2-Br-1-CB_{11}H_{11}]^-$ and the aqueous solution was extracted three times with diethyl ether (40 mL). The combined ether extracts were evaporated to dryness and the colorless oil was dissolved in water (50 mL). After addition of a solution of $[Me_4N]^+[Cl]^-$ (0.5 g, 4.6 mmol) in $H_2O$ (20 mL), the white pure $[Me_4N]^+[2-Br-1-CB_{11}H_{11}]^-$ was filtered and dried in vacuum to yield (0.3 g, 19%).

Attempted Synthesis of $[CB_{11}H_{12}]^-$ using $CI_2$ produced $[Me_4N]^+[7-OH-B_{11}H_{13}]^-$: $CI_2$ from $CHI_3+NaH$ (CHI 3 acted as an oxidizing agent and no $CI_2$ insertion was observed). In a 250 mL two-neck flask $[Me_3NH]^+[B_{11}H_{14}]^-$ (1 g, 5.2 mmol) was dissolved in THF (20 mL) under an argon atmosphere. The solution was cooled to −78° C., and NaH (95%) (0.9 g, 40 mmol) was added. After stirring 15 min at room temperature, the THF and the $Me_3N$ was removed in vacuum. THF (40 mL) was added to the residue and the suspension was cooled to −78° C., and $CHI_3$ (6 g, 15.3 mmol) was added.

The reaction mixture was stirred over night at room temperature. Ethanol (10 mL) and water (50 mL) were added, the THF and the ethanol were removed in vacuum. The solution was acidified by addition of 10% HCl. After filtration $[Me_4N]^+[Cl]^-$ (0.57 g, 5.2 mmol) in $H_2O$ (20 mL) was added to the filtrate and the white precipitate was filtered and dried in vacuum. The residue was crystallized from $CH_3CN/H_2O$, to yield colorless crystals of $[Me_4N]^+$ $[7-OH-B_{11}H_{13}]^-$ (290 mg, 25%).

Synthesis of $[Me_4N]^+[4-R-C_6H_4-1-CB_{11}H_{11}]^-$ (R=H, F): PhCCl from $PhCHCl_2$. In a 250 mL two-neck flask $[Me_3NH]^+[B_{11}H_{14}]^-$ (1 g, 5.2 mmol) was dissolved in dry THF (10 mL) under an argon atmosphere. The solution was cooled to 0° C., and NaH (95%) (1.2 g, 53 mmol) was added. After stirring 15 min at room temperature, the THF and the $Me_3N$ were removed in vacuum. THF (20 mL) was added to the residue and the suspension was cooled to 0° C., and a mixture of $(4-R-C_6H_4-CHCl_2)$ (2 mL, 15.3 mmol, R=H) (2 mL, 14.9 mmol, R=F) and ethanol (1.5 mL) was added slowly.

The reaction mixture was stirred overnight at room temperature, and EtOH (3 mL) was added slowly. After addition of water (50 mL), the THF and the EtOH were removed in vacuum and the solution was transferred to a separation funnel where residual $(4-R-C_6H_4-CHCl_2)$ (R=H,F) was separated from the aqueous layer. $[Me_3NH]^+Cl^-$ (1 g, 10 mmol) was added to the water layer, and a white precipitate was separated and dried under reduced pressure. The residue was dissolved in methanol (6 mL) and filtered. The filtrate was injected on a HPLC column and a 58/42 MeOH/$H_2O$ mixture was used to elute the $[4-R-C_6H_4-1-CB_{11}H_{11}]^-$ (R=H, $R_F$=21.5; R=F, $R_F$=28.3) product.

Methanol was removed under reduced pressure, the aqueous solution was extracted three times with diethyl ether (40 mL), the combined ether extracts were evaporated to dryness and the colorless oil was dissolved in water (50 mL). After addition of a solution of $[Me_4N]^+[Cl]^-$ (0.5 g, 4.6 mmol) in $H_2O$ (20 mL), the white precipitate was filtered and dried under reduced pressure to yield pure $[Me_4N]^+[4-R-C_6H_4-1-CB_{11}H_{12}]^-$ (R=H, F) (293 mg, 19%, R=H; 330 mg, 18%, R=F).

Synthesis of $[NMe_4]^+[(4-C_6H_5-C_6H_4)-1-CB_{11}H_{11}]^-$. In a 250 mL two-neck flask $[Me_3NH]^+[B_{11}H_{14}]^-$ (1 g, 5.2 mmol) was dissolved in dry THF (10 mL) under an argon atmosphere. The solution was cooled to 0° C., and NaH (95%) (1.5 g, 66 mmol) was added carefully. After stirring 15 min at room temperature, THF and $NMe_3$ were removed under reduced pressure. THF (20 mL) was added to the residue and the suspension was cooled to 0° C., and a mixture of $p-C_6H_5-C_6H_4CHCl_2$ (2.37 g, 10.0 mmol) and ethanol (2.0 mL) was added slowly. The reaction mixture was stirred overnight at room temperature, and EtOH (3 mL) was added slowly. After addition of water (50 mL), THF and the EtOH were removed under reduced pressure and the solution was transferred to a separation funnel where residual $p-C_6H_5-C_6H_4CHCl_2$ was separated from the aqueous layer. $[Me_4N]^+[Cl]^-$ (1 g, 9.2 mmol) was added to the water layer, and a white precipitate was separated and dried under reduced pressure to yield $[NMe_4]^+[closo-1-(p-

$C_6H_5$—$C_6H_4$)—$CB_{11}H_{11}$]$^-$ (537 mg, 28%). MS (z/e): 295. NMR: $^{11}B\{^1H\}$: −7.6 (12), −12.9 (2–11); $^1H$: 7.60–7.22 (m) Ph.

Synthesis of $[NMe_4]^+[(4-Br—C_6H_4)-1-CB_{11}H_{11}]^-$. In a 250 mL two-neck flask $[Me_3NH]^+[B_{11}H_{14}]^-$ (1 g, 5.2 mmol) was dissolved in dry THF (10 mL) under an argon atmosphere. The solution was cooled to 0° C., and NaH (95%) (1.5 g, 66 mmol) was added carefully. After stirring 15 min at room temperature, THF and $NMe_3$ were removed under reduced pressure. THF (20 mL) was added to the residue and the suspension was cooled to 0° C., and a mixture of p-Br—$C_6H_4CHCl_2$ (2.40 g, 10.0 mmol) and ethanol (2.0 mL) was added slowly. The reaction mixture was stirred overnight at room temperature, and EtOH (3 mL) was added slowly. After addition of water (50 mL), THF and the EtOH were removed under reduced pressure and the solution was transferred to a separation funnel where residual p-$BrC_6H_4CHCl_2$ was separated from the aqueous layer. $[Me_4N]^+[Cl]^-$ (1 g, 9.2 mmol) was added to the water layer, and a white precipitate was separated and dried under reduced pressure to yield $[NMe_4]^+[closo-1-(p-Br—C_6H_4)—CB_{11}H_{11}]^-$ (369 mg, 19%). NMR: $^{11}B\{^1H\}$: −8.1 (12), −13.1 (2–11); $^1H$: 7.21–6.97 (m) Ph.

Synthesis of $[PPh_4]^+[(4-I—C_6H_4)-1-CB_{11}H_{11}]^-$. In a 250 mL two-neck flask $[Me_3NH]^+[B_{11}H_{14}]^-$ (1 g, 5.2 mmol) was dissolved in dry THF (10 mL) under an argon atmosphere. The solution was cooled to 0° C., and NaH (95%) (1.5 g, 66 mmol) was added carefully. After stirring 15 min at room temperature, THF and $NMe_3$ were removed under reduced pressure. THF (20 mL) was added to the residue and the suspension was cooled to 0° C., and a mixture of p-I—$C_6H_4CHCl_2$ (2.87 g, 10.0 mmol) and ethanol (2.0 mL) was added slowly. The reaction mixture was stirred overnight at room temperature, and EtOH (3 mL) was added slowly. After addition of water (50 mL), THF and the EtOH were removed under reduced pressure and the solution was transferred to a separation funnel where residual p-$IC_6H_4CHCl_2$ was separated from the aqueous layer. $[Me_4N]^+[Cl]^-$ (1 g, 9.2 mmol) was added to the water layer, and a white precipitate was separated and dried under reduced pressure. A small amount (157 mg) of the residue was dissolved in methanol (4 mL) and filtered. The filtrate was injected on a HPLC column and a 60/40 MeOH/$H_2O$ mixture was used to elute the [closo-1-(p-$IC_6H_4$)—$CB_{11}H_{11}$]$^-$($R_F$=17.2) product. Methanol was removed under reduced pressure, the aqueous solution was extracted three times with diethyl ether (15 mL), the combined ether extracts were evaporated to dryness, and the colorless oil was dissolved in water (15 mL). After addition of a solution of $[PPh_4]^+[Cl]^-$ (375 mg, 1 mmol), the white precipitate was filtered and dried under reduced pressure to yield pure $[PPh_4]^+[closo-1-(p-IC_6H_4)—CB^{11}H_{11}]^-$ (21 mg, 3%). NMR: $^{11}B\{^1H\}$: −7.5 (12), −12.8 (2–11); $^1H$: 7.49–7.26 (m) Ph.

Synthesis of $[Me_4N]^+[7-OH—B_{11}H_{13}]^-$. When the synthesis of [1-Ph-$CB^{11}H^{11}$]$^-$: PhCCl from $PhCCl_3$ was attempted $[Me_4N]^+[7-OH—B_{11}H_{13}]^{31}$ was formed since E $PhCCl_3$ acted as an oxidizing agent and not as a carbene generating agent. In a 250 mL two-neck flask $[Me_3NH]^+[B_{11}H_{14}]^-[1]$ (1 g, 5.2 mmol) was dissolved in THF (20 mL) under an argon atmosphere. The solution was cooled to −78° C. and n-BuLi (10 ML, 16 mmol) was added dropwise. After stirring 1 h at room temperature, the solution was cooled to −78° C. and $C_6H_5CCl_3$ (1 mL, 7 mmol) was added, and the reaction mixture was heated overnight under reflux. After cooling to room temperature, the THF was removed in vacuum and the residue was taken up in 25 mL of water, and the solution was acidified by addition of 10% HCl. $[Me_4N]^+$ Cl$^-$ (1 g, 9.1 mmol) was added and a white solid precipitated. The solid was filtered and dried in vacuum to yield colorless $[Me_4N]^+[7-OH—B_{11}H_{13}]^-$ (250 mg, 22%).

The use of Other Starting Boranes in Addition to $[B_{11}H_{14}]^-$:

We have observed carbon insertion into $B_{10}H_{14}$ and into its degradation product, $[B_9H_{14}]^-$. These experiments are only preliminary; yields and selectivity of product formation can be improved with methods known in the art.

Synthesis of $[Me_4N]^+[nido-1-Cl-1-CB_9H_{12}]^-$ and $[Me_4N]^+[closo-1-CB_{10}H_{11}]^-$: $CCl_2$ from $CHCl_3$+NaOEt/ NaH with $B_{10}H_{14}$ (under the reaction condition $B_{10}H_{14}$ partly degraded to $[B_9H_{14}]^-$; carbene insertion occurred into $B_{10}H_{14}$ to give [closo-1-$CB_{10}H_{11}$]$^-$ and into $[B_9H_{14}]^-$ to give [nido-1-Cl-1-$CB_9H_{12}$]$^-$; modification of reaction conditions will allow selectivity). In a 250 mL two-neck flask $B_{10}H_{14}$ (611 mg, 5 mmol) was dissolved in THF (40 mL) and NaH (95%) (1.2 g, 53 mmol) was added at 0° C. After stirring 15 min at room temperature, the mixture was cooled to 0° C. and $CHCl_3$ (2 mL, 24 mmol) was added. After stirring for 1 h at room temperature, EtOH (3 mL) was added dropwise and the stirring was continued for another 2 h. After addition of water (50 mL), the THF and EtOH were removed in vacuum, the solution was acidified with 10% HCl, and a white solid precipitated by addition of $[Me_4N]^+$ Cl$^-$ (1 g, 9.1 mmol) and dried in vacuum to yield a colorless mixture of $[Me_4N]^+[B_9H_{14}]^-$ (343 mg, 40%), $[Me_4N]^+$ [nido-1-Cl-1-$CB_9H_{12}$]$^-$ (172 mg, 15%) and $[Me_4N]^+$[closo-1-$CB_{10}H_{11}$]$^-$ (110 mg, 11%), as determined by $^{11}B$ NMR.

The residue was dissolved in methanol (6 mL) and filtered. The filtrate was injected on an HPLC and a 48/52 MeOH/$H_2O$ mixture was used to separate the [nido-1-Cl-1-$CB_9H_{12}$]$^-$ ($R_F$=29.5) and the [closo-1-$CB_{10}H_{11}$]$^-$ $^{(R}F$=17.9) carborane products from the borane $[Me_4N]^+[B_9H_{14}]^-$.

Methanol was removed under reduced pressure from the [nido-1-Cl-1-$CB_9H_{12}$]$^-$ fraction, the residual aqueous solution was extracted three times with diethyl ether (40 mL) and the organic layers were separated from the aqueous layer. The combined ether extracts were evaporated to dryness and the colorless oil was dissolved in water (50 mL). After addition of a solution of $[Me_4N]^+[Cl]^-$ (0.5 g, 4.6 mmol) in $H_2O$ (20 mL), the white pure $[Me_4N]^+[nido-Cl-1-CB_9H_{12}]^-$ was filtered and dried under reduced pressure (127 mg, 11%).

Methanol was removed under reduced pressure from the [closo-1-$CB_{10}H_{11}$]$^-$ fraction, the aqueous solution was extracted three times with diethyl ether (40 mL), the combined ether extracts were evaporated to dryness and the colorless oil was dissolved in water (50 mL). After addition of a solution of $[Me_4N]^+[Cl]^-$ (0.5 g, 4.6 mmol) in $H_2O$ (20 mL), the white pure $[Me_4N]^+[closo-1-CB_{10}H_{11}]^-$ was filtered and dried under reduced pressure (80 mg, 8%).

Synthesis of $[Me_3NH]^+[nido-1-(4-F-C_6H_4)-1-CB_9H_{12}]^-$: 4-F—$C_6H_4$-CCl from 4F—$CH_6H_4$—$CHCl_2$+NaOEt/NaH with $B_{10}H_{14}$ (note: the base degraded $B_{10}H_{14}$ to $[B_9H_{14}]^-$, which then reacted with the carbene; much of it was left over; conditions could clearly be improved by one of ordinary skill in the art—after a complete conversion of $B_{10}H_{14}$ to $[B_9H_{14}]^-$ the carbene can be added in quite good yield). In a 250 mL two neck flask $B_{10}H_{14}$ (611 mg, 5 mmol) was dissolved in THF (40 mL) and at 0° C. NaH (95%) (1.2 g, 53 mmol) was added. After stirring 15 min at room temperature, the mixture was cooled at 0° C. and a mixture of 4-F—$C_6H_4$—$CHCl_2$ (2 mL, 14.9 mmol) and EtOH (1.9 mL) was added dropwise. After stirring for 1 h at room temperature, EtOH (3 mL) was added dropwise and the mixture was stirred for another 2 h. After addition of water (50 mL) the THF and EtOH were removed under reduced pressure, the solution was acidified with 10% HCl, and [Me$_4$N]$^+$Cl$^-$ (1 g, 9.1 mmol) was added. A white solid precipitated and was dried in vacuum to yield a colorless mixture of [Me$_4$N]$^+$[B$_9$H$_{14}$]$^-$ (343 mg, 40%), and [Me$_4$N]$^+$ [nido-1-(4-F—C$_6$H$_4$)-1-CB$_9$H$_{12}$] (190 mg, 13%, as determined by $^{11}$B NMR analysis).

The residue was dissolved in methanol (6 mL) and filtered. The filtrate was injected on an HPLC column and a 58/42 MeOH/H$_2$O mixture was used to separate [nido-1-(4-F—C$_6$H$_4$)-1-CB$_9$H$_{12}$]$^-$ (R$_F$=34.1) from [B$_9$H$_{14}$]$^-$ (R$_F$=29.8). Methanol was removed under reduced pressure from the [nido-1-(4-F—C$_6$H$_4$)-1-CB$_9$H$_{12}$]$^-$ fraction, the aqueous solution was extracted three times with diethyl ether (40 mL). The combined ether extracts were evaporated to dryness and the colorless oil was dissolved in water (50 mL). After addition of a solution of [Me$_4$N]$^+$[Cl]$^-$ (0.5 g, 4.6 mmol) in H$_2$O (20 mL), the white pure [Me$_4$N]$^+$[nido-1-(4-F—C$_6$H$_4$)-1-CB$_9$H$_{12}$]$^-$ was filtered and dried in vacuum to yield (145 mg, 10%).

Attempted insertion of CCl$_2$ into B$_{10}$H$_{14}$: CCl$_2$ from CHCl$_3$+NaOH with B$_{10}$H$_{14}$ (resulted in formation of [Me$_3$BH]$^+$[B$_9$H$_{14}$]$^-$ by degradation of B$_{10}$H$_{14}$).

In a 250 mL two neck flask B$_{10}$H$_{14}$ (611 mg, 5 mmol) was dissolved in 2N NaOH (50 mL) and after addition of CHCl$_3$ (3 mL, 36 mmol) the reaction mixture was stirred over night at room temperature.

The solution was acidified by addition of 10% HCl and after addition of [Me$_3$NH]$^+$Cl$^-$ (1 g, 10 mmol) a pale yellow solid precipitated and dried in vacuum to yield colorless [Me$_3$NH]$^+$[B$_9$H$_{14}$]$^-$ (670 mg, 78%).

Below, the chemical equations for the new synthesis of CB$_{11}$H$_{12}^-$ from B$_{11}$H$_{14}^-$ and its old synthesis from B$_{10}$H$_{14}$ are summarized.

Synthesis of [Me$_3$NH]$^+$[CB$_{11}$H$_{12}$]$^-$. In a 500 mL three-neck flask Me$_3$NH$^+$B$_{11}$H$_{14}^-$ (5 g, 0.026 mol) was dissolved in THF (50 mL) under argon atmosphere. The solution was cooled to 0° C. and NaH (95%, 2.61 g, 0.10 moles) was added slowly. After stirring for 30 min at 0° C. the cooling was removed and the mixture was evaporated to dryness under reduced pressure and THF (120 mL) was added. NaOEt (8.80 g, 0.13 moles) was added to the reaction flask and the mixture was again cooled to 0° C. CHCl$_3$ (6.20 mL, 0.08 mol) was added over a period of 5 h. The reaction mixture was stirred for 8 h at 0° C. Water (100 mL) was added and THF was evaporated under reduced pressure. The solution was acidified by the addition 10% HCl (40 mL). Residual THF and EtOH were removed under reduced pressure. Charcoal (2 g) was added to the solution and the solid material was filtered off. Upon the addition of Me$_3$NHCl to the supernatant (5 g, 0.05 mol) a white solid precipitated. The solid was dried under reduced pressure to yield Me$_3$NH$^+$CB$_{11}$H$_{12}^-$ (2.20g, 41%) of approximately 93% purity.

Although the description above contains many specificities, these are intended as illustrations of the presently-preferred embodiments of the invention, not as limitations. All references cited herein are hereby incorporated by reference to the extent not inconsistent with the disclosure herewith.

Synthesis of [CB$_{11}$H$_{12}$]$^-$ from B$_{11}$H$_{14}^-$

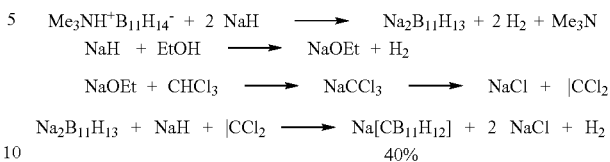

Byproduct: Na[2-Cl-CB$_{11}$H$_{11}$] 2%

Synthesis of B$_{11}$H$_{14}^-$ from NaBH$_4$

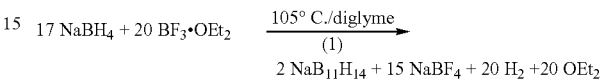

Synthesis of [CB$_{11}$H$_{12}$]$^-$ from B$_{10}$H$_{14}$

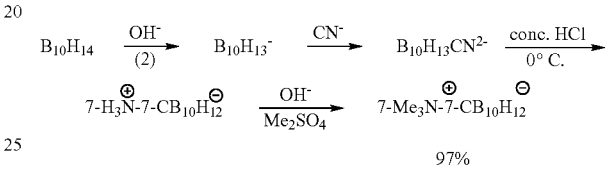

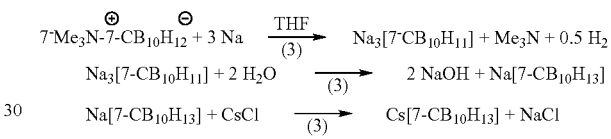

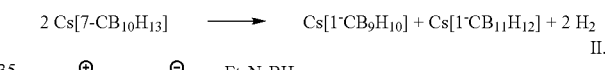

I.

II.

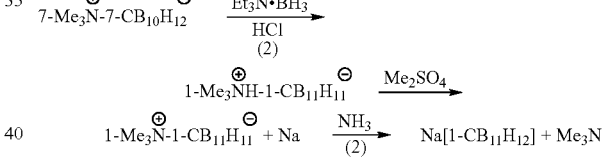

REFERENCES (1) Dunks, G. B.; and Ordonez, K. P.; Inorg. Chem., 1978, 17, 1514.
(2) Plešek, J.; Jelínek, T.; Drdáková, E.; Heřmánek, S. and Štíbr, B.; Collect. Czech. Chem. Commun., 1984, 49 1559.
(3) Knoth, W. H.; Little, J. L.; Lawrence, J. R.; Scholer, F. R. and Todd, L. J.; Inorg. Synth., 1968, 11, 33.

We claim:

1. A method for making a carborane anion of formula

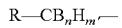

where R is H, a halide, a phenyl group or a substituted phenyl group, n is an integer ranging from (5–11) which comprises the step of reacting a substituted carbene of formula:

Y$^1$Y$^2$C:

where Y$^1$ and Y$^2$ can be any of H, a halide, a phenyl group or substituted phenyl group with a borane anion of formula:

in the presence of a strong base, wherein n, m and m' are integers, n ranging from 5 to 11 and m and m' ranging from 5 to 16 and wherein the relative values of n, m and m' depend upon the exact structure of the borane starting material.

2. The method of claim 1 wherein the strong base is hydride.

3. The method of claim 1 wherein the strong base is an alkyllithium compound.

4. The method of claim 1 wherein the strong base is not a nitrogen base.

5. The method of claim 1 wherein the carbene is dihalocarbene and R is H.

6. The method of claim 5 wherein the carbene is dichlorocarbene.

7. The method of claim 1 wherein the borane anion is provided as an $Na^+$ salt.

8. The method of claim 1 wherein the borane anion is provided as an ammonium salt.

9. The method of claim 8 wherein any amine generated during reaction is substantially removed.

10. The method of claim 1 wherein the borane anion is at least partially solubilized in solvent.

11. The method of claim 1 wherein the solvent is TBF, DME or diglyme.

12. The method of claim 1 wherein the carbene is $PhY^2C$: where $Y^2$ is a halide and the carborane anion formed is $Ph\text{-}CB_nH_n^-$ where Ph is a phenyl or a substituted phenyl group.

13. The method of claim 1 wherein the carborane is $CB_{11}H_{12}^-$.

14. The method of claim 1 wherein the carborane is $R\text{—}CB_{11}H_{12}^-$ and R is not hydrogen.

15. The method of claim 13 wherein the carbene is $PhY^2C$: $Y^2$ is a halide and the carborane is $Ph\text{-}CB_{11}H_{12}^-$ where Ph is a phenyl group or a substituted phenyl group.

16. A method for making the carborane anion $CB_nH_{m'}$ which comprises reacting the anion $B_nH_{m'-1}^{2-}$ with a carbene.

17. The method of claim 16 wherein the carborane anion is $CB_{11}H_{12}^-$ and the carbene is a dihalocarbene.

18. A method for making the carborane anion $CB_{11}H_{12}^-$ which comprises the steps of:

reacting a borane anion of formula

$B_{11}H_{14}^-$ with a carbene of formula $Y^1Y^2C$:, where $Y^1$ and $Y^2$ can be any of H, a halide, a phenyl group or substituted phenyl group, in the presence of a strong base.

19. The method of claim 18 wherein the strong base is an alkyllithium compound.

20. The method of claim 18 wherein the carbene is a dihalocarbene.

21. The method of claim 18 wherein the carbene is dichlorocarbene.

22. A method for making the carborane anion

$CB_{11}H_{12}^-$ which comprises the step of providing a solution containing the borane anion $B_{11}H_{14}^-$ and a strong base, generating a carbene of formula $Y^1Y^2C$:, where $Y^1$ and $Y^2$ can be any of H, a halide, a phenyl or a substituted phenyl group, in the solution to react to form the carborane anion.

23. The method of claim 22 further comprising isolating the carborane anion as a salt.

24. The method of claim 23 wherein the carborane anion is isolated by precipitation of a carborane anion salt from solutions.

25. The method of claim 24 wherein the carborane anion salt is an ammonium salt.

26. The method of claim 18 wherein the strong base is hydride.

* * * * *